United States Patent
Kim et al.

(10) Patent No.: US 12,318,401 B2
(45) Date of Patent: *Jun. 3, 2025

(54) INJECTABLE SHEAR-THINNING HYDROGEL CONTAINING THERAPEUTIC AGENT FOR ENHANCED TUMOR THERAPY

(71) Applicants: MAYO FOUNDATION FOR MEDICAL EDUCATION AND RESEARCH, Rochester, MN (US); THE REGENTS OF THE UNIVERSITY OF CALIFORNIA, Oakland, CA (US); BOSTON SCIENTIFIC SCIMED, INC., Maple Grove, MN (US)

(72) Inventors: Hanjun Kim, Los Angeles, CA (US); Chun Xu, Los Angeles, CA (US); Ehsan Jabbarzadeh, Columbia, SC (US); Rahmi Oklu, Chandler, AZ (US); Alireza Khademhosseini, Los Angeles, CA (US)

(73) Assignees: MAYO FOUNDATION FOR MEDICAL EDUCATION AND RESEARCH, Rochester, MN (US); The Regents of the University of California, Oakland, CA (US); Boston Scientific Scimed, Inc., Maple Grove, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 17/956,701

(22) Filed: Sep. 29, 2022

(65) Prior Publication Data
US 2023/0093831 A1   Mar. 30, 2023

Related U.S. Application Data (60) Provisional application No. 63/250,441, filed on Sep. 30, 2021, provisional application No. 63/249,949, filed on Sep. 29, 2021.

(51) Int. Cl.
| A61K 31/704 | (2006.01) |
| A61K 9/06 | (2006.01) |
| A61K 9/51 | (2006.01) |
| A61K 47/42 | (2017.01) |
| A61K 47/69 | (2017.01) |
| A61P 35/00 | (2006.01) |

(52) U.S. Cl.
CPC ............ *A61K 31/704* (2013.01); *A61K 9/06* (2013.01); *A61K 9/5115* (2013.01); *A61K 9/5169* (2013.01); *A61K 47/42* (2013.01); *A61K 47/6933* (2017.08); *A61P 35/00* (2018.01)

(58) Field of Classification Search
CPC ...... A61K 31/704; A61K 9/06; A61K 9/5115; A61K 9/5169; A61K 47/42; A61K 47/6933; A61K 35/13; A61K 47/02; A61K 9/0024; A61K 38/00; A61P 35/00; C08J 2389/00; C08J 3/075
See application file for complete search history.

(56) References Cited

U.S. PATENT DOCUMENTS

| 2005/0227910 A1 | 10/2005 | Yang et al. |
| 2010/0120149 A1 | 5/2010 | Kim et al. |
| 2012/0315265 A1 | 12/2012 | Lai et al. |
| 2014/0302051 A1 | 10/2014 | Askari et al. |
| 2017/0043058 A1 | 2/2017 | Oreffo et al. |
| 2018/0104059 A1 | 4/2018 | Roche et al. |
| 2018/0360920 A1 | 12/2018 | Khademosseini et al. |
| 2019/0290804 A1 | 9/2019 | Askari et al. |

FOREIGN PATENT DOCUMENTS

| WO | 2016123573 A1 | 8/2016 |
| WO | 2017069822 A2 | 4/2017 |
| WO | 2018053273 A1 | 3/2018 |
| WO | 2020198504 A1 | 10/2020 |
| WO | 2021061837 A1 | 4/2021 |

OTHER PUBLICATIONS

Cimen et al. Injectable and Self-Healable pH-Responsive Gelatin-PEG/Laponite Hybrid Hydrogels as Long-Acting Implants for Local Cancer Treatment. ACS Applied Polymer Materials, 3(7), 3504-3518. https://doi.org/10.1021/acsapm.1c00419 (Year: 2021).*
Sheikhi, A., Afewerki, S., Oklu, R., Gaharwar, A. K., & Khademhosseini, A. Effect of ionic strength on shear-thinning nanoclay-polymer composite hydrogels. Biomaterials Science, 6(8), 2073-2083. https://doi.org/10.1039/c8bm00469b (Year: 2018).*
Xue et al. Synthesis of Injectable Shear-Thinning Biomaterials of Various Compositions of Gelatin and Synthetic Silicate Nanoplatelet. Biotechnology Journal, 15(8). https://doi.org/10.1002/biot.201900456 (Year: 2020).*
International Search Report and Written Opinion dated Jan. 23, 2023 for International Application No. PCT/US2022/045273.
Lee, "pH-responsive Doxorubicin Delivery using Shear-Thinning Biomaterials for Localized Melanoma Treatment", Biometrics Research, vol. 22, Article 27, 2018.

(Continued)

*Primary Examiner* — Yih-Horng Shiao
*Assistant Examiner* — Hoi Yan Lee
(74) *Attorney, Agent, or Firm* — Seager, Tufte & Wickhem, LLP (57) ABSTRACT

We have developed novel shear-thinning biomaterials using silica nanoparticles, gelatin-based polymers and small molecules such as doxorubicin. Shear-thinning biomaterial technology offers enables polymers and drugs loaded inside such polymers to be easily delivered directly through catheters into target area for use, for example, in cancer therapy and immunotherapy. When a force above a certain threshold is applied to inject such materials, they "thin" and behaves as a semi-solid, allowing the material to readily flow through a catheter. When the force is removed, the material instantly becomes a soft solid with significant cohesive properties that prevent it from dislodging or breaking up.

18 Claims, 7 Drawing Sheets

(56) References Cited

OTHER PUBLICATIONS

Thambi et al., "Injectable hydrogels for sustained release of therapeutic agents", J Control Release, 267:57-66, Dec. 10, 2017 doi: 10.1016/j.jconrel.2017.08.006. Epub Aug. 4, 2017.

Gianonni et al., "Rheological properties, biocompatibility and in vivo performance of new hydrogel-based bone fillers", Biomater. Sci., Issue 4, 1691-1703, 2016.

Guvendiren et al., "Shear-thinning hydrogels for biomedical applications," Soft Matter pp. 260-272, 2012, 8.

Purcell et al., "Injectable and bioresponsive hydrogels for on-demand matrix metalloproteinase inhibition," Nat Mater 2014, 13, 653-661.

Jahan et al., "One-step fabrication of apatite-chitosan scaffold as a potential injectable construct for bone tissue engineering: An investigation of structural property," Carbohyd Polym 2019, 203, 60-70.

Yang et al., "In situ-forming injectable hydrogels for regenerative medicine," Prog Polym Sci 2014, 39, 1973-1986.

Yang et al., "Composite hydrogel beads based on chitosan and Laponite: preparation, swelling, and drug release behaviour," 2011. (Blocked From Iran).

Su et al., "Enhancing the Gelation and Bioactivity of Injectable Silk Fibroin Hydrogel with Laponite Nanoplatelets," ACS Appl Mater Interfaces 2016, 8, 9619-9628.

Mulyasasmita et al., "Avidity-controlled delivery of angiogenic peptides from injectable molecular-recognition hydrogels," Tissue Eng Part A 2014, 20, 2102-2114.

Whitlow et al., "Polymeric Nanohybrids as a New Class of Therapeutic Biotransporters," Macromolecular Chemistry and Physics 2016, 217, 1245-1259.

Paul et al., "Injectable graphene oxide/hydrogel-based angiogenic gene delivery system for vasculogenesis and cardiac repair," ACS Nano 2014, 8, 8050-8062.

Higuchi et al., "Biomaterials used in stem cell therapy for spinal cord injury," Progress in Materials Science 2019, 103, 374-424.

Tomas et al., "Laponite (R) : A key nanoplatform for biomedical applications?," Nanomed-Nanotechnol 2018, 14, 2407-2420.

Dawson et al., "Clay Gels For the Delivery of Regenerative Microenvironments," Adv Mater 2011, 23, 3304-+.

Dawson et al., "Clay: New Opportunities for Tissue Regeneration and Biomaterial Design," Adv Mater 2013, 25, 4069-4086.

Xavier et al., "Bioactive nanoengineered hydrogels for bone tissue engineering: a growth-factor-free approach," ACS Nano 2015, 9, 3109-3118.

Bhatnagar et al., "Hyaluronic Acid and Gelatin Clay Silica nanoparticles based STB: Substrates for Cell Adhesion and Controlled Drug Delivery," Journal of Chemical and Biological Interfaces 2014, 2, 34-44.

Li et al., "pH sensitive Laponite/alginate hybrid hydrogels: swelling behaviour and release mechanism," Soft Matter 2011, 7, 6231-6238.

Hardy et al., "Biomimetic conducting polymer-based tissue scaffolds," Curr Opin Biotechnol 2013, 24, 847-854.

Gaharwar et al., "Shear-thinning nanosilica nanoparticles based STB for the treatment of hemorrhage," ACS Nano 2014, 8, 9833-9842.

Gaharwar et al., "2D Nanoclay for Biomedical Applications: Regenerative Medicine, Therapeutic Delivery, and Additive Manufacturing," Adv Mater 2019, 31, e1900332.

Gaharwar et al., "Bioactive Silicate Nanoplatelets for Osteogenic Differentiation of Human Mesenchymal Stem Cells," Adv Mater 2013, 25, 3329-3336.

Park et al., "Injectable biodegradable hydrogel composites for rabbit marrow mesenchymal stem cell and growth factor delivery for cartilage tissue engineering," Biomaterials 2007, 28, 3217-3227.

Avery et al., "An injectable shear-thinning biomaterial for endovascular embolization," Sci Transl Med 2016, 8, 365ra156.

Moore et al., "Development of a shear-thinning biomaterial as an endovascular embolic agent for the treatment of type B aortic dissection," J Mech Behav Biomed Mater 2019, 99, 66-77.

Kerativitayanan et al., "Nanoengineered Osteoinductive and Elastomeric Scaffolds for Bone Tissue Engineering," ACS Biomaterials Science & Engineering 2017, 3, 590-600.

Hasany et al., "Combinatorial Screening of Nanoclay-Reinforced Hydrogels: A Glimpse of the "Holy Grail" in Orthopedic Stem Cell Therapy?," ACS Applied Materials & Interfaces 2018, 10, 34924-34941.

Wilson et al., "Shear-Thinning and Thermo-Reversible Nanoengineered Inks for 3D Bioprinting," ACS Appl Mater Interfaces 2017, 9, 43449-43458.

Samimi et al., "Smart Shear-Thinning Hydrogels as Injectable Drug Delivery Systems," Polymers (Basel) 2018, 10.

Sheikhi et al., "Effect of ionic strength on shear-thinning nanoclay-polymer silica nanoparticles based STB," Biomaterials Science 2018, 6, 2073-2083.

Ren et al., "Injectable hydrogel based on quaternized chitosan, gelatin and dopamine as localized drug delivery system to treat Parkinson's disease," International journal of biological macromolecules 2017, 105, 1079-1087.

International Search Report and Written Opinion dated Mar. 2, 2023 for International Application No. PCT/US2022/045265.

\* cited by examiner

INJECTABLE SHEAR-THINNING HYDROGEL CONTAINING THERAPEUTIC AGENT FOR ENHANCED TUMOR THERAPY

CROSS-REFERENCE TO RELATED APPLICATIONS

This application claims the benefit of U.S. Provisional Patent Application Ser. No. 63/249,949 filed on Sep. 29, 2021 and U.S. Provisional Patent Application Ser. No. 63/250,441 filed on Sep. 30, 2021. These provisional applications are incorporated herein by reference.

STATEMENT REGARDING FEDERALLY SPONSORED RESEARCH AND DEVELOPMENT

This invention was made with government support under Grant Numbers HL137193 and HL140951, awarded by The National Institutes of Health. The government has certain rights in the invention.

TECHNICAL FIELD

The present invention relates to shear thinning biomaterials comprising bioactive agents and methods for making and using them.

BACKGROUND OF THE INVENTION

Shear-thinning hydrogels are non-Newtonian materials that behave as viscous fluids under shear stress and then recover solid-like properties upon elimination of the stress [1]. Due to these properties, injectable shear-thinning biomaterials (STB) are attracting attention as a group of self-healing materials that allow for fluent infusion and local equilibrium after approaching the final application site. In clinical applications, STBs can be delivered into the body using a needle or a general/microcatheter by manual pressure [2-4]. To optimize the clinical application, it is necessary to adjust the physical properties of STB according to the specific clinical situations. By changing the physical properties, one can synthesize tailored hydrogels for specific clinical applications, such as embolizing a certain size of blood vessel, controlled drug release, and modulation of the stiffness of tissue engineering scaffolds.

The physical properties of conventional STBs can be modulated by a combination of several carbon-based, polymeric, and inorganic nanomaterials [5-8]. Several biomaterials, such as gelatin, hyaluronic acid, chitosan, collagen, and alginate have been previously used along with inorganic constituents to form STBs [14-17]. In particular, gelatin limits the adsorption of nonspecific proteins, enhanced hemolysis, and ultimately prolongs clotting time, demonstrating substantially improved hemocompatibility of STB in vitro [18]. Furthermore, the application of gelatin in tissue engineering and regenerative medicine has been approved by the Food and Drug Administration (FDA) [19-21]. Conventional STBs are prepared by mixing gelatin with synthetic clay nanoparticles, LAPONITE®, for hemostasis and endovascular embolization [18, 22]. These STBs exhibit strong shear-thinning behavior as well as biocompatible properties ranging from blood coagulation to minimized inflammatory response. Others have extended this work to implement STBs as embolic agents [23], functionalized scaffolds [24, 25], 3D-bioinks [26] and drug delivery systems [27]. Unfortunately, however, synthetic clay nanoparticles such as LAPONITE are crystallized nanoparticles and the size, surface chemistry are not easily tuned. In addition, the biocompatibility of LAPONITE in various in vivo uses needs to be further investigated, a fact which complicates its use in clinical applications.

For the reasons noted above, there is a need in the art for new shear-thinning materials and methods for making and using them.

SUMMARY OF THE INVENTION

As discussed below, we have developed novel shear-thinning biomaterials using spherical silica nanoparticles, gelatin-based polymers and small molecule therapeutic agents. As an illustrative working embodiment, we developed a doxorubicin-loaded injectable shear thinning biomaterials (STB) using silicate nanoplatelet (LAPONITE XLG) and gelatin-based polymers. Shear-thinning biomaterial technology offers unique properties enabling drugs loaded inside to be easily delivered directly through needles or catheters into target area. We focused on the fact that shear thinning biomaterial is 1) injectable and easy to apply, and 2) exhibits high localization due to the high mechanical stability after injection. Therefore, in this working embodiment, we loaded anti-cancer drug, doxorubicin to the shear thinning material to treat solid tumors.

The invention disclosed herein has a number of embodiments. Embodiments of the invention include, for example, a composition of matter comprising a polymeric gelatin, silicate nanoparticles and a therapeutic agent having a molecular weight less than 1000 Daltons. In such compositions, amounts of the gelatin, the silicate nanoparticles and the therapeutic agent are selected to form a shear thinning hydrogel. In certain embodiments of the invention, the composition comprises from about 1% (w/w) to about 5% (w/w) polymeric gelatin (e.g., ranging anywhere from about 1% (w/w) to about 2% (w/w) to about 3% (w/w) to about 4% (w/w) to about 5% (w/w) polymeric gelatin) (in other words, ranging between any two of the preceding numerical values), and from about 1% (w/w) to about 5% (w/w) silicate nanoparticles (e.g., ranging anywhere from about 1% (w/w) to about 2% (w/w) to about 3% (w/w) to about 4% (w/w) to about 5% (w/w) silicate nanoparticles).

In certain embodiments of the invention, the composition comprises from about 0.5% (w/w) to about 85% (w/w) polymeric gelatin and silicate nanoparticles (e.g., ranging anywhere from about 0.5% (w/w) to about 1% (w/w) to about 2% (w/w) to about 5% (w/w) to about 10% (w/w) to about 25% (w/w) to about 50% (w/w) to about 75% (w/w) to about 85% (w/w) gelatin and silicate nanoparticles). In certain embodiments of the invention, the ratio of the silicate nanoparticles to the polymeric gelatin is from about 1.0 to about 0.1 (e.g., ranging anywhere from about 1.0 to about 0.9 to about 0.8 to about 0.7 to about 0.6 to about 0.5 to about 0.4 to about 0.3 to about 0.2 to about 0.1). In certain embodiments, the polymeric gelatin is methacrylated gelatin (GelMA), acrylated gelatin, or thiolated gelatin. In certain embodiments, the composition comprises about 0.5% (w/w) to about 99% (w/w) water (e.g., ranging anywhere from about 0.5% (w/w) to about 1% (w/w) to about 2% (w/w) to about 5% (w/w) to about 10% (w/w) to about 25% (w/w) to about 50% (w/w) to about 75% (w/w) to about 90% (w/w) to about 95% (w/w) to about 97.5% (w/w) to about 99% (w/w) water). In certain embodiments, the composition comprises from about 0.01% (w/w) to about 20% (w/w) of the therapeutic agent (e.g., ranging anywhere from about 0.01% (w/w) to about 0.02% (w/w) to about 0.5% (w/w) to about 1% (w/w) to about 2% (w/w) to about 5% (w/w) to about 10% (w/w) to about 15% (w/w) to about 20% (w/w) of the therapeutic agent).

Typically, these compositions further comprise a pharmaceutical excipient selected from the group consisting of a preservative, a tonicity adjusting agent, a detergent, a viscosity adjusting agent, a sugar and a pH adjusting agent. In some embodiments of the invention, the composition further comprises a human cancer cell. The compositions of the invention include one or more small molecule therapeutic agents such as an anti-inflammatory agent, an agent that modulates coagulation, an antibiotic agent, a chemotherapeutic agent or the like. Exemplary therapeutic agents include: alkaloids such as paclitaxel, vinblastine, and vincristine; antimetabolites such as gemcitabine, 5-fluoruracil, and methotrexate; antibiotics and antibiotic derivatives such as doxorubicin, daunorubicin, and bleomycin; and hormonal antineoplastics such as tamoxifen, diethylstilbestrol, and polyestradiol phosphate. In certain illustrative embodiments of the invention, the therapeutic agent is doxorubicin.

In some embodiments of the invention, amounts of the components are such that when disposed in an environment having a pH of 7.4, less than 15% or 20% of agent is released from the shear thinning hydrogel over a period of 15 days; and when disposed in in an environment having a pH of 5.0, more than 15% or 20% is released from shear thinning hydrogel over a period of 15 days. In certain embodiments of the invention, the shear thinning hydrogel requires an injection force of at least 5 newtons but less than 30 newtons to extrude the shear thinning hydrogel from a 2.4 Fr Catheter/1 cc syringe.

Yet another embodiment of the invention is a method of making a shear-thinning biocompatible composition disclosed herein comprising combining together spherical silica nanoparticles, gelatin and a small therapeutic molecule such as doxorubicin, and optionally a pharmaceutical excipient so as to form a shear-thinning biocompatible composition. In certain embodiments of these methods, a surface property of the spherical silica nanoparticles, a median diameter of the spherical silica nanoparticles, a relative amount of spherical silica nanoparticles; and/or a relative amount of gelatin or the like is selected to tune or modulate one or more rheological properties or therapeutic agent release profile of the shear-thinning biocompatible composition. By modulating the mechanical properties of the compositions of the invention in this manner, embodiments of the invention can be tailored for use in a variety of different clinical applications.

Another embodiment of the invention is a method of delivering a shear-thinning biocompatible composition disclosed herein to a preselected site (e.g. an in vivo location comprising cancer cells). Typically, such methods comprise disposing the composition in a vessel having a first end comprising an opening and a second end (e.g. a catheter); applying a force to the second end of the vessel, wherein the force is sufficient to liquify the composition; and then delivering the composition out of the vessel through the opening and to the preselected site. In some embodiments, the vessel comprises a syringe loaded with the composition, the syringe configured for fluid communication with a needle and/or a catheter tube. Embodiments of such methods include treatment regimens that use a shear-thinning biocompatible composition disclosed herein to deliver a therapeutic agent. In certain embodiments, the present disclosure is directed to method of treating a solid tumor in a subject in need thereof, comprising administering to the subject a therapeutically effective amount of a shear-thinning biocompatible composition disclose herein. In certain embodiments, the solid tumor is selected from a blood vessel tumor, brain tumor (e.g., meningioma or glioblastoma), spinal tumor, carotid body tumor, liver cancer, lung cancer, neuroendocrine tumor, renal tumor, pancreatic tumor or prostatic tumor. In certain embodiments, the solid tumor is selected from skin cancer (e.g., melanoma, mast cell tumor, squamous cell carcinoma, or basal cell tumor), breast cancer, sarcomatous tumor (e.g., fibrosarcoma, leiomyosarcoma, rhabomyo sarcoma, osteosarcoma, or chondrosarcoma), and lymphomatous tumor. In certain embodiments, the composition is administered to a localized area in need of treatment. In certain embodiments, the composition provides sustained release of a therapeutically effective amount of the therapeutic agent to the localized area. In certain embodiments, the localized area comprises a solid tumor. In certain embodiments, the composition provides tumor embolization and sustained release of a therapeutically effective amount of the therapeutic agent to the tumor.

Other objects, features and advantages of the present invention will become apparent to those skilled in the art from the following detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modifications.

DETAILED DESCRIPTION OF THE INVENTION

In the description of embodiments, reference may be made to the accompanying figures which form a part hereof, and in which is shown by way of illustration a specific embodiment in which the invention may be practiced. It is to be understood that other embodiments may be utilized, and structural changes may be made without departing from the scope of the present invention. Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the aspects of the techniques and procedures described or referenced herein are well understood and commonly employed by those skilled in the art. The following text discusses various embodiments of the invention.

Shear-thinning biomaterial (STB) technology offers unique properties enabling a solid polymer and drugs loaded inside to be easily delivered directly through means such as catheters into a target area. In view of this, we have developed a class of novel shear-thinning biomaterials using silica nanoparticles and gelatin-based polymers. Embodiments of the invention include, for example, a shear-thinning biocompatible composition of matter comprising silica nanoparticles and gelatin. Among inorganic composite compositions, silica is classified as "Generally Recognized As Safe (GRAS)" FDA, and is considered one of the most biocompatible materials. In view of this, silicate nanoparticles have been employed in pharmaceutical, cosmetic and food industries as active ingredients or rheological modifiers due to their uniform particle size with electrical surface charges and bioactive properties [9, 10]. In addition, the size, structure, surface properties of silica nanoparticles can be easily tuned, properties which allow silica nanoparticles to provide a class of materials that are useful in a wide variety of biomedical applications.

The compositions of the invention can include further constituents such as additional polymers, excipients, therapeutic agents and the like. For example, compositions of the invention can include one or more Food and Drug Administration (FDA) approved or cytocompatible polymers. Such polymers include alginate, chitosan, collagen, hyaluronic acid (HA), chondroitin sulfate (ChS), dextrin, gelatin, fibrin, peptide, and silk. Synthetic polymers such as poly(ethylene glycol) (PEG), poly(ethylene oxide) (PEO), poloxamer (Pluronic®) (PEO-PPO-PEO), polyoxamine (Tetronic®) (PEO-PPO), poly(vinyl alcohol) (PVA), poly(lactic-co-glycolic acid) (PLGA), poly(glycolic acid) (PGA), poly(lactic acid) (PLA), polycaprolactone (PCL), poly(L-glutamic acid) (PLga), polyanhydrides, poly(N-isopropylacrylamide) (PNIPAAm), polyaniline and the like can also be included in compositions of the invention. As is known in the art, preparations of hydrogels can be made to include either chemically or physically crosslinked materials.

Certain embodiments of the compositions of the invention include, for example a pharmaceutical excipient such as one selected from the group consisting of a preservative, a tonicity adjusting agent, a detergent, a viscosity adjusting agent, a sugar and a pH adjusting agent. For compositions suitable for administration to humans, the term "excipient" is meant to include, but is not limited to, those ingredients described in Remington: The Science and Practice of Pharmacy, Lippincott Williams & Wilkins, 21st ed. (2006) the contents of which are incorporated by reference herein.

Optionally, the compositions of the invention include one or more small molecule therapeutic agents (i.e. ones having a molecular weight less 1000 Daltons) such as an anti-inflammatory agent, an agent that modulates coagulation, an antibiotic agent, a chemotherapeutic agent or the like. In a working embodiment of the invention disclosed herein, the small molecule therapeutic agent is doxorubicin. Compositions of the invention can be formulated for use as carriers or scaffolds of therapeutic agents such as drugs, cells, proteins, and bioactive molecules (e.g., enzyme). As carriers, such compositions can incorporate the agents and deliver them to a desired site in the body for the treatments of a variety of pathological conditions. These include, for example, infectious and inflammatory diseases (e.g. Parkinson's disease, bacterial and antimicrobial infection, diabetes and the like) as well as cancers (e.g. colon, lung, breast, ovarian, lymphoma cancers and the like). In addition, as scaffolds, compositions of the invention can provide a flexible dwelling space for cells and other agents for use in tissue repair and the regeneration of desired tissues (e.g. for cartilage, bone, retina, brain, and, neural tissue repair, vascular regeneration, wound healing and the like). Moreover, embodiments of the invention can include immunomodulatory agents useful for immunotherapy in order to, for example, enhance components of the immune system. Certain illustrative materials and methods that can be adapted for use in such embodiments of the invention are found, for example in Hydrogels: Design, Synthesis and Application in Drug Delivery and Regenerative Medicine 1st Edition, Singh, Laverty and Donnelly Eds; and Hydrogels in Biology and Medicine (Polymer Science and Technology) UK ed. Edition by J. Michalek et al.

Embodiments of the invention include, for example, a composition of matter comprising a polymeric gelatin, silicate nanoparticles and a therapeutic agent having a molecular weight less than 1000 Daltons. In such compositions, amounts of the gelatin, the silicate nanoparticles and the therapeutic agent are selected to form a shear thinning hydrogel. In certain embodiments of the invention, the composition comprises from about 1% to about 5% polymeric gelatin, and from about 1% to about 5% silicate nanoparticles. Typically, these compositions further comprise a pharmaceutical excipient selected from the group consisting of a preservative, a tonicity adjusting agent, a detergent, a viscosity adjusting agent, a sugar and a pH adjusting agent. In some embodiments of the invention, the composition further comprises a human cancer cell. In illustrative embodiments of the invention, the therapeutic agent is doxorubicin.

Figure 3A:
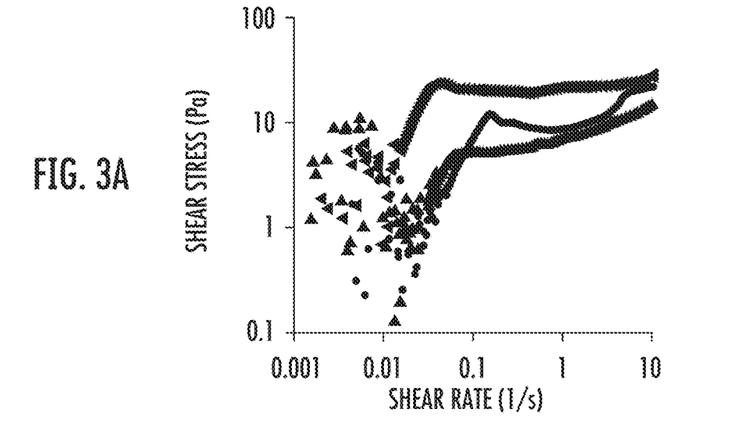
FIG. 3A, FIG. 3B, and FIG. 3C show the rheological properties of various compositions of STBs.
Figure 3B:
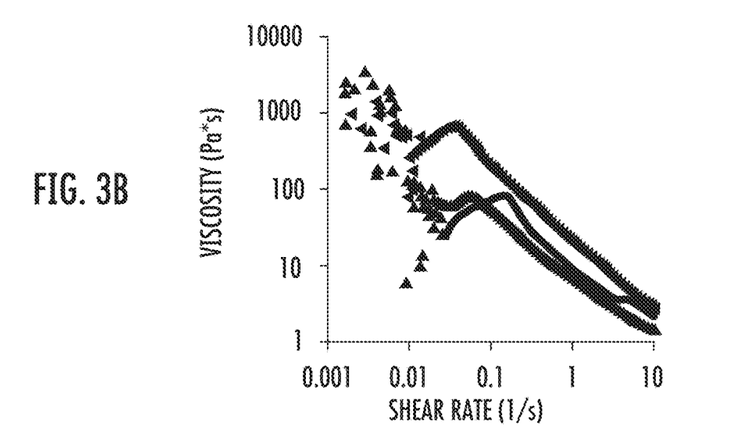
Figure 3C:
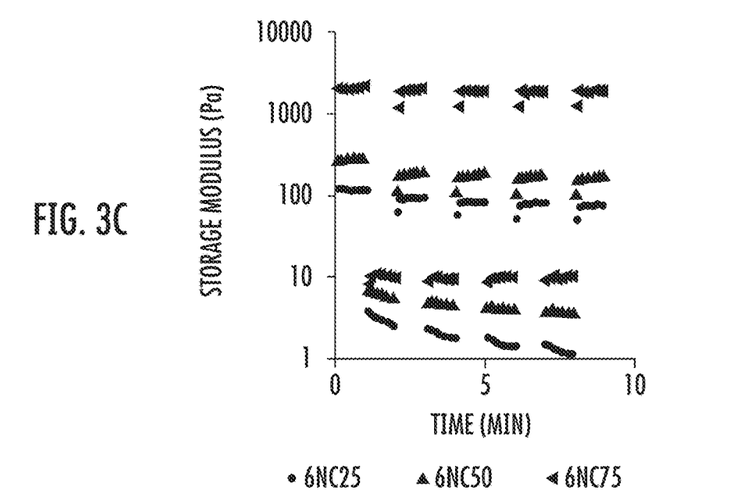

In some embodiments of the invention, the composition is disposed within a vessel (e.g. a catheter) selected for its ability to facilitate a user modulating one or more rheological properties of the composition. Certain illustrative materials and methods that can be adapted for use in embodiments of the invention are found, for example in Biomedical Hydrogels: Biochemistry, Manufacture and Medical Applications (Woodhead Publishing Series in Biomaterials) 1st Edition; Steve Rimmer (Editor). As shown in FIGS. 3A-3C, illustrative embodiments of the invention, the components of the composition are selected to provide desirable rheological properties.

Another embodiment of the invention is a method of delivering a shear-thinning biocompatible composition disclosed herein to a preselected site (e.g. an in vivo location where an individual has experienced trauma or injury or exhibits a pathology such as a cancer). Typically, such methods comprise disposing the composition in a vessel having a first end comprising an opening and a second end (e.g. a catheter); applying a force to the second end of the vessel, wherein the force is sufficient to liquify the composition; and then delivering the composition out of the vessel through the opening and to the preselected site. Embodiments of such methods include treatment regimens that use a shear-thinning biocompatible composition disclosed herein to deliver a therapeutic agent as shown, for example, in FIGS. 4A-4C.

Yet another embodiment of the invention is a method of making a shear-thinning biocompatible composition disclosed herein comprising combining together silica nanoparticles and gelatin, a small molecule therapeutic agent and optionally a pharmaceutical excipient so as to form a shear-thinning biocompatible composition. In certain embodiments of these methods, a surface property of the silica nanoparticles, a median diameter of the silica nanoparticles, a relative amount of silica nanoparticles; and/or a relative amount of gelatin or the like is selected to tune or modulate one or more rheological properties of the shear-thinning biocompatible composition. By modulating the mechanical properties of the compositions of the invention in this manner, embodiments of the invention can be tailored for use in a variety of different clinical applications. In this context, a wide variety of art accepted materials and methods can be adapted for use in embodiments of the invention, for example those disclosed in U.S. Patent Publication Nos.: 20050227910, 20100120149, 20120315265, 20140302051 and 20190290804; and Lee, Biomaterials Research volume 22, Article number: 27 (2018); Thambi et al., J Control Release. 2017 Dec. 10; 267:57-66. doi: 10.1016/j.jconrel.2017.08.006. Epub 2017 Aug. 4; and Gianonni et al., Biomater. Sci., 2016, the contents of which are incorporated by reference.

Illustrave Materials and Methods of the Invention

As an illustrative working embodiment of the invention, we developed a doxorubicin-loaded injectable shear thinning biomaterials (STB) using silicate nanoplatelet (LAPONITE XLG) and gelatin-based polymers. Shear-thinning biomaterial technology offers unique properties enabling drugs loaded inside to be easily delivered directly through needles or catheters into target area. We focused on the fact that shear thinning biomaterial is 1) injectable and easy to apply, and 2) exhibits high localization due to the high mechanical stability after injection. Therefore, we loaded anti-cancer drug, doxorubicin to the shear thinning material to treat solid tumor.

Figure 1A:
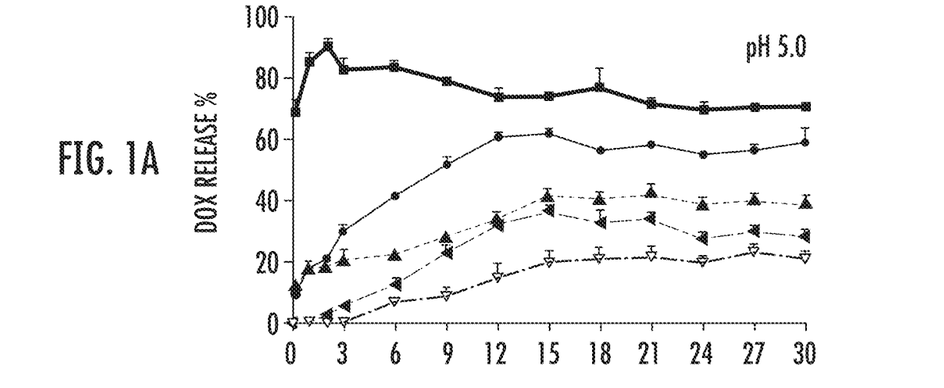
FIG. 1A, FIG. 1B and FIG. 1C show release profile data from various compositions of doxorubicin-loaded STBs under different pH conditions.
Figure 1B:
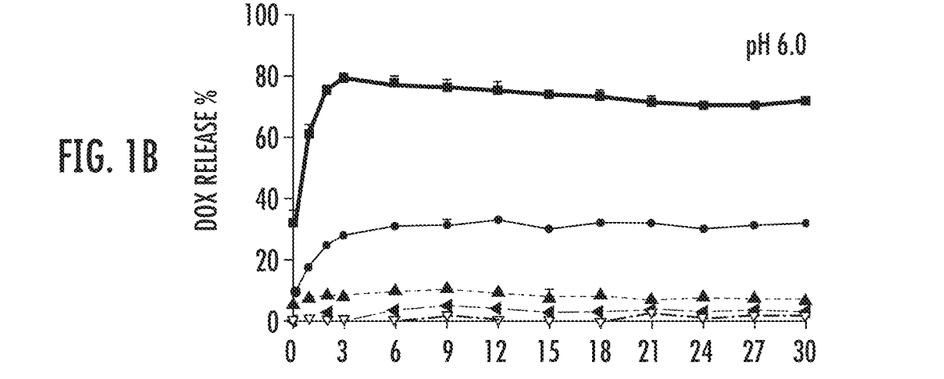
Figure 1C:
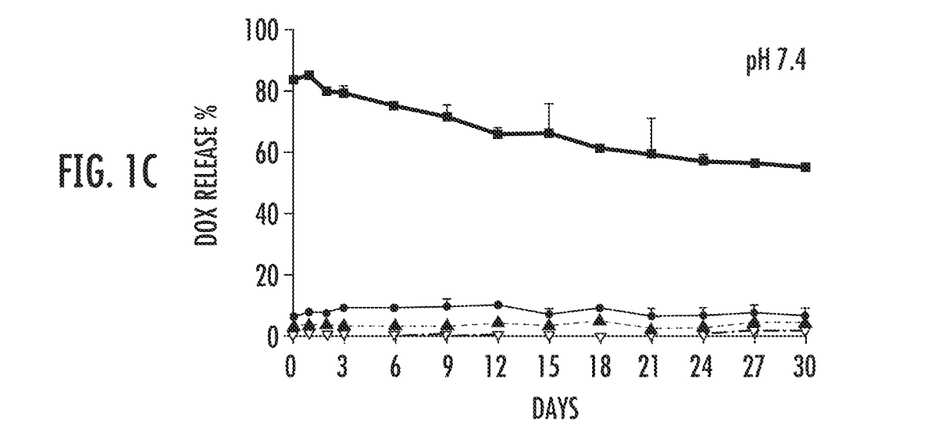
Figure 2A:
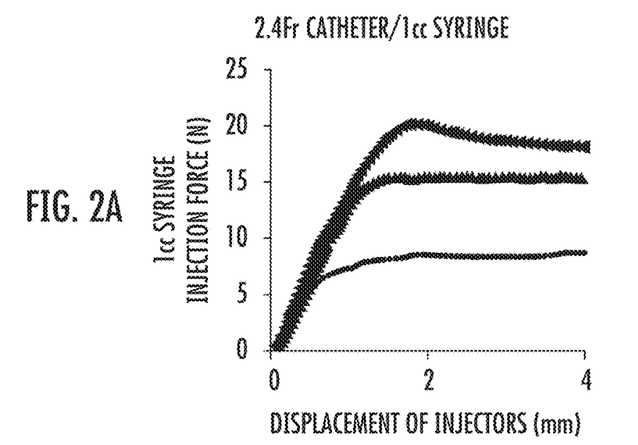
FIG. 2A, FIG. 2B and FIG. 2C show injection force data from various compositions of STBs.
Figure 2B:
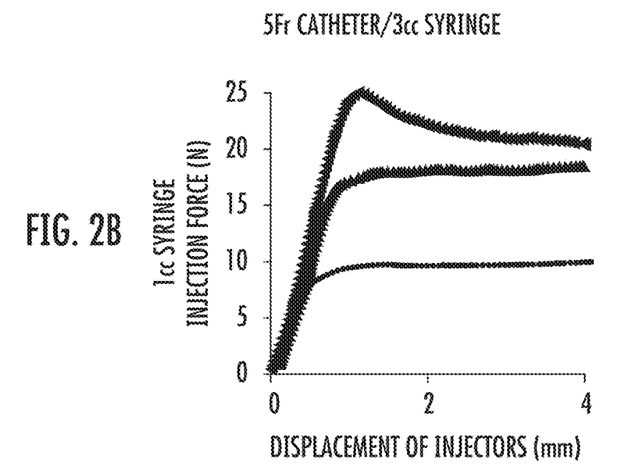
Figure 2C:
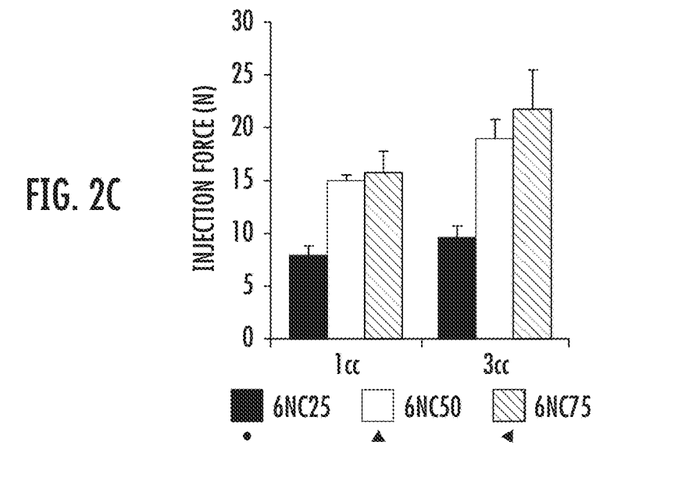

We tested three different STB compositions (Gelatin 4.5%/LAPONITE 1.5% [6NC25]; Gelatin 3.0%/LAPONITE 3.0% [6NC50]; Gelatin 1.5%/LAPONITE 4.5% [6NC75]) for the doxorubicin-loading biomaterials. The release profile was analyzed for 30 days under the three pH conditions (pH 5.0, 6.0, 7.4) (FIGS. 1A, 1B, 1C). Gelatin released doxorubicin within 3 days regardless of pH condition, while LAPONITE released less than 20% of doxorubicin only in acidic condition. Interestingly, all three STB compositions showed high release of doxorubicin under acidic conditions at pH 5, but little release at 7.4, which is normal physiological pH. It was also observed that the higher the LAPONITE ratio, the lower the release of doxorubicin. Injection force measurement showed that all three compositions we tested could be delivered via a 2.4 Fr microcatheter and a 5 Fr general catheter (FIGS. 2A, 2B, 2C). All STB compositions were within favorable injection force range (<30N), but the higher the LAPONITE content, the higher the injection force. Rheological measurements found that all STB compositions exhibit shear thinning properties (non-Newtonian behavior, decreasing viscosity upon shear rate increase) and the storage modulus is higher with higher LAPONITE content (FIGS. 3A, 3B, 3C).

Figure 4A:
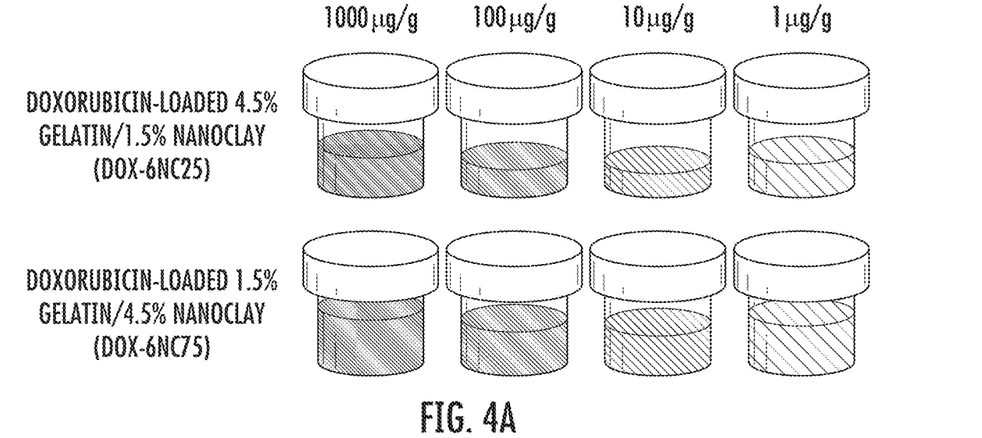
FIG. 4A shows photographs of various doxorubicin-loaded STBs.
Figure 4B:
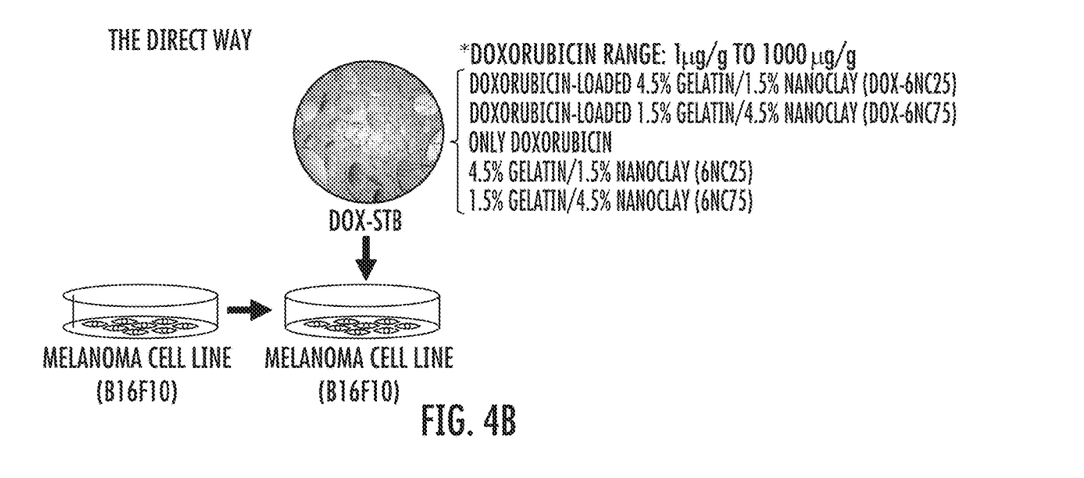
FIG. 4B provides a schematic illustration of in vitro study for assessing direct-contact anti-cancer effect of doxorubicin-loaded STBs.
Figure 4C:
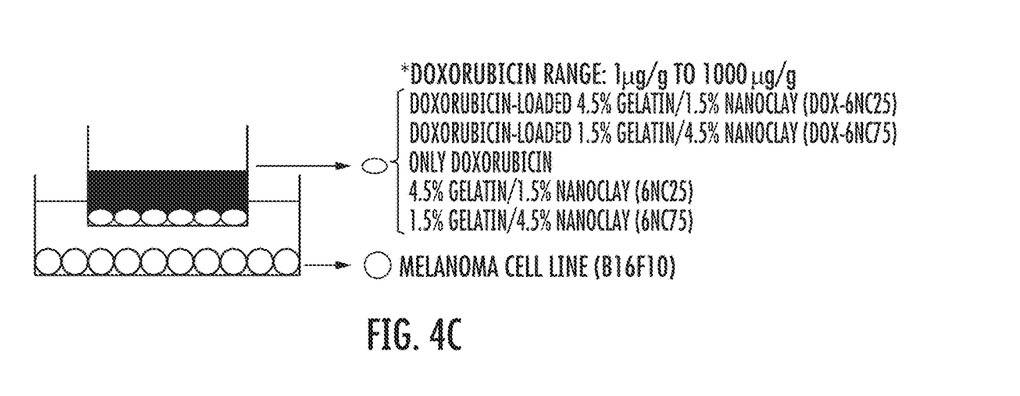
FIG. 4C provides a schematic illustration of in vitro study for assessing anti-cancer effect of doxorubicin-loaded STBs through transwell release.
Figure 5A:
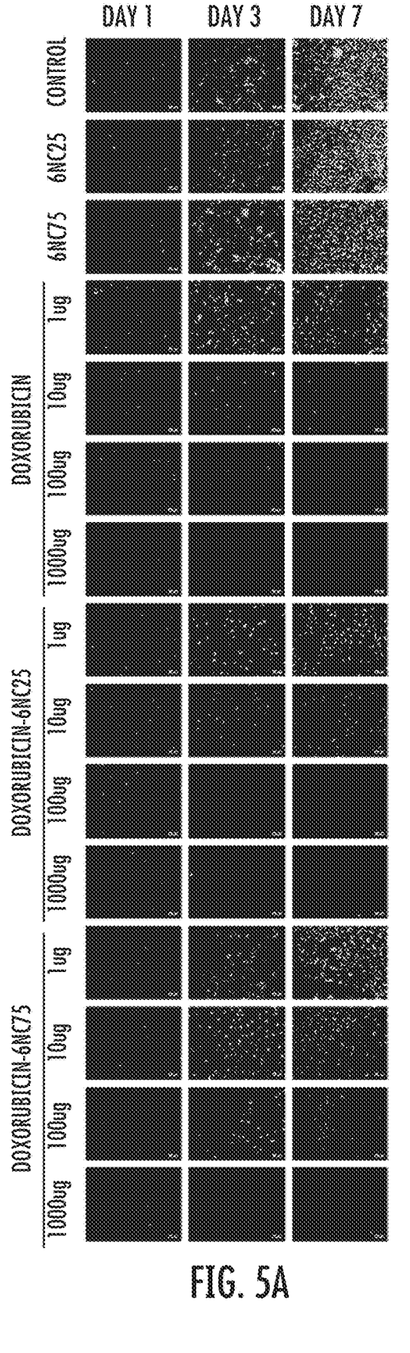
FIG. 5A, FIG. 5B and FIG. 5C show data from an in vitro anti-cancer efficacy evaluation through direct-contact of doxorubicin-loaded STBs.
Figure 5B:
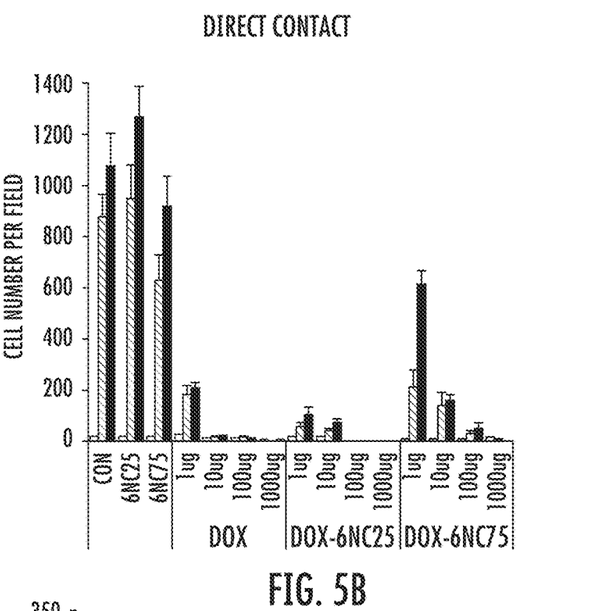
Figure 5C:
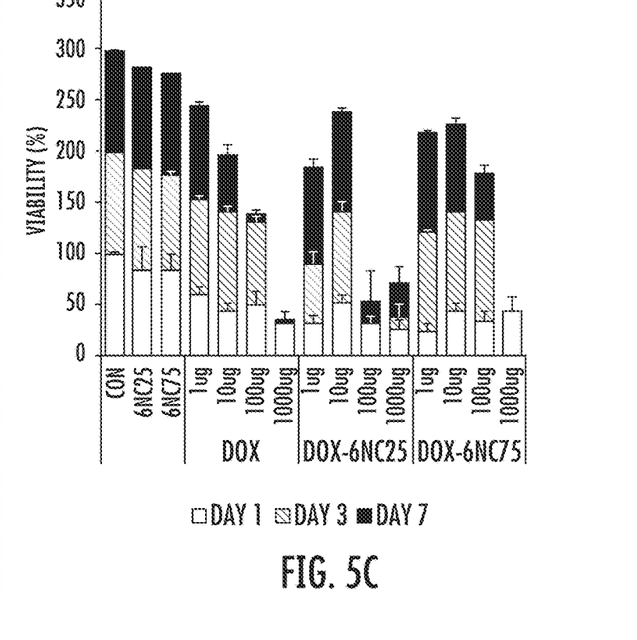
Figure 6A:
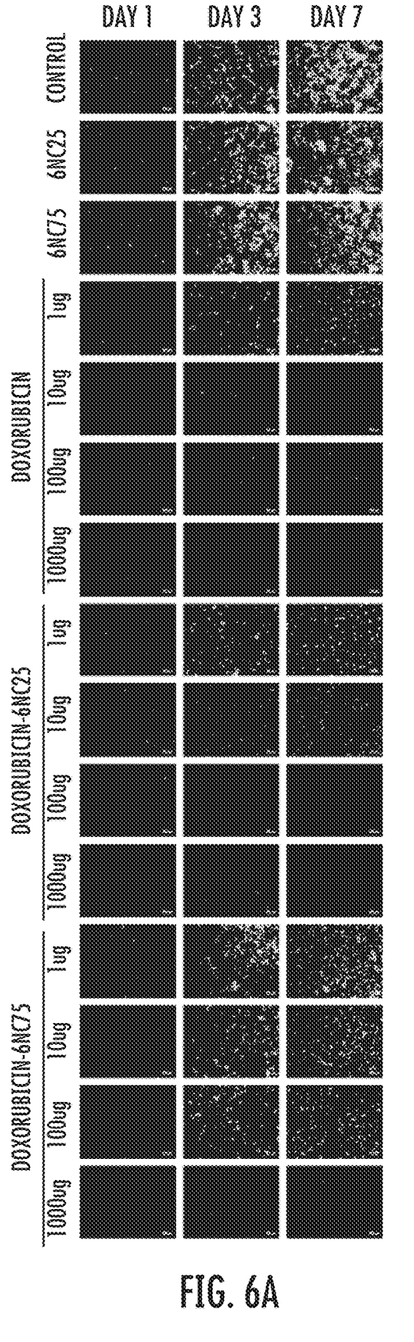
FIG. 6A, FIG. 6B and FIG. 6C shows data from an in vitro anti-cancer efficacy evaluation through transwell release of doxorubicin-loaded STBs.
Figure 6B:
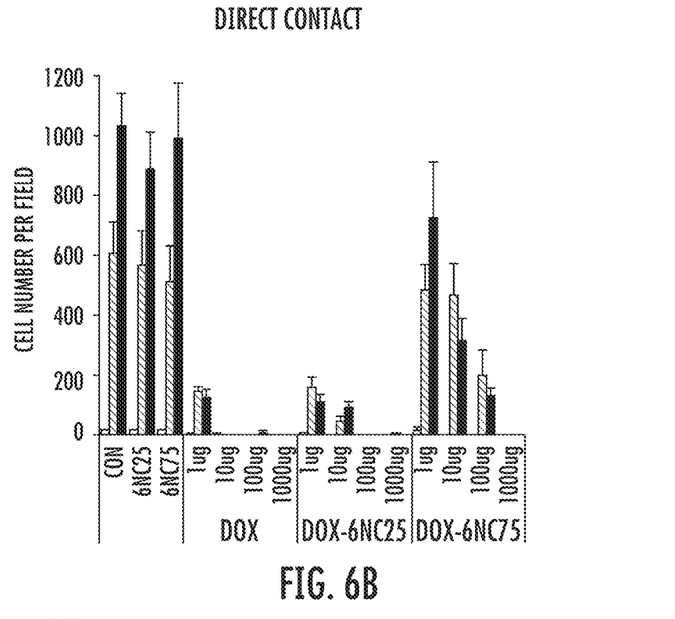
Figure 6C:
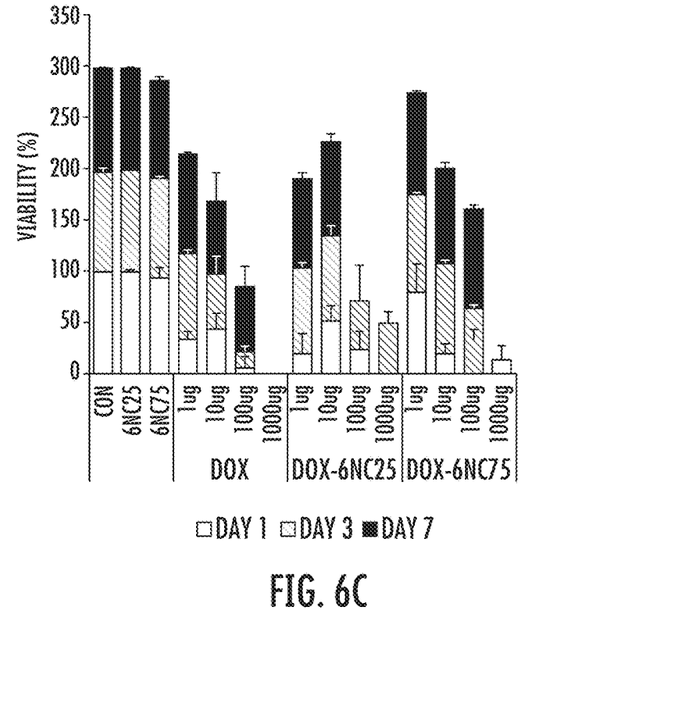

We prepared two types of STB by mixing gelatin polymer and LAPONITE, and then added doxorubicin solution to make doxorubicin-loaded STB (DOX-STB) (FIG. 4A). To determine the in vitro anti-cancer efficacy of DOX-STB, we devised two types of in vitro tests. First, to analyze the anticancer efficacy of DOX-STB in contact with tumor, B16F10 melanoma cells were seeded on the culture plate, and then applied two STBs loaded with four ranges of doxorubicin (FIG. 4B). Other in vitro models were identified using a transwell release anticancer efficacy model to analyze anticancer efficacy due to doxorubicin released from DOX-STB rather than direct contact. (FIG. 4C). Both direct contact and transwell release in vitro models were analyzed for anticancer efficacy by performing live dead staining after 1, 3 and 7 days of DOX-STB application. Direct contact in vitro anti-cancer efficacy analysis showed that STB itself did not show anti-cancer effects, whereas most tumor cells were killed at a concentration of 10 ug/g or more of doxorubicin (FIGS. 5A, 5B, 5C) Similarly, indirect transwell release results showed that tumor cells were killed at 10 ug/g or more of DOX-STB (FIGS. 6A, 6B, 6C).

Figure 7A:
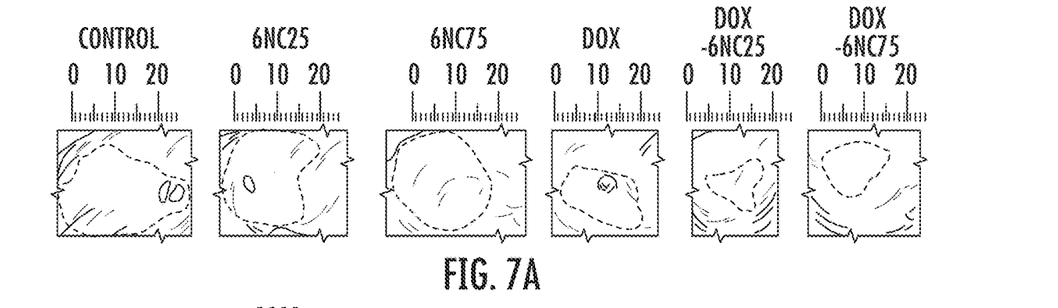
FIG. 7A shows data from an in vivo anti-cancer efficacy study of DOX-STB for melanoma.
Figure 7B:
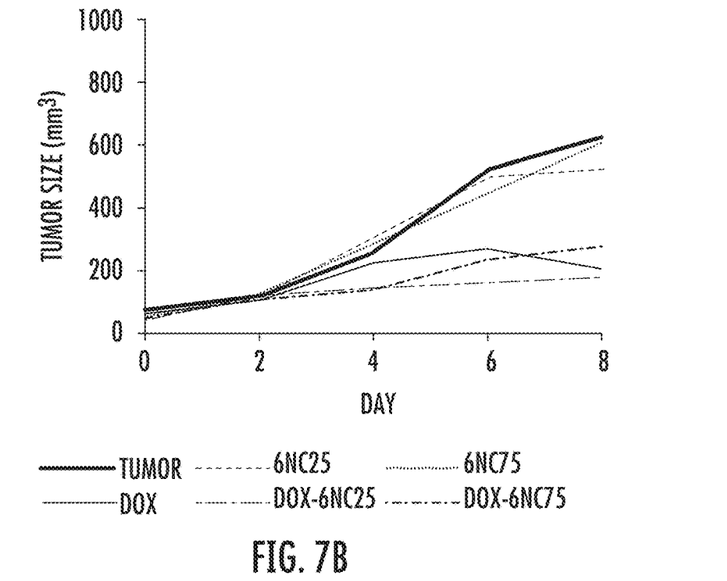
FIG. 7B shows data from a tumor growth curve for the melanoma-bearing mouse with doxorubicin-loaded STBs.
Figure 7C:
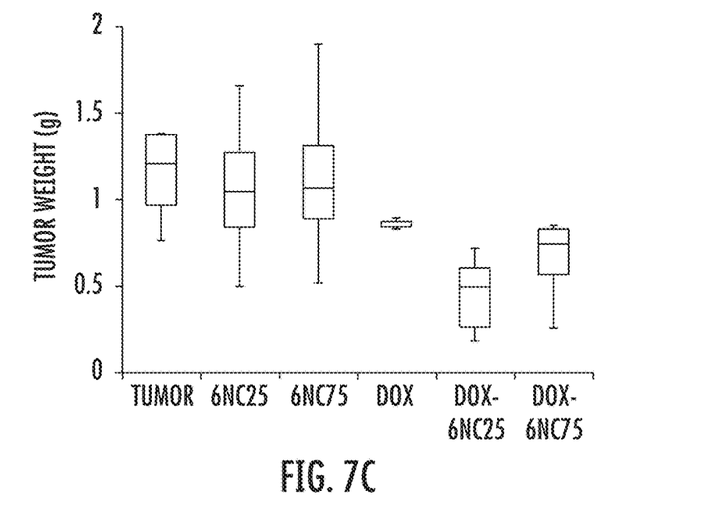
FIG. 7C shows data from a tumor weight study on the day of sacrifice

Finally, in vivo anti-cancer efficacy of DOX-STB was analyzed in a melanoma tumor model made by subcutaneous injection of B16F10 melanoma tumor cells into C57B1/6J mice (FIG. 7A). In gross, similar to in vitro experiments, STB itself did not show anti-cancer efficacy, while tumor size decreased in all groups loaded with doxorubicin (DOX, DOX-6NC25, DOX-6NC75). On the tumor growth curve measured by caliper every two days, both doxorubicin-loaded groups were found to inhibit melanoma growth (FIG. 7B). Interestingly, median tumor weights of DOX-6NC25 and DOX-6NC75 were less than DOX in tumor weight (FIG. 7C).

Taken together, our DOX-STB shows 1) pH-dependent doxorubicin release (doxorubicin release at acidic pH), 2) that DOX release is adjustable according to STB composition change, and 3) that direct and/or released doxorubicin from DOX-STB could kill the tumor cells, and 4) that DOX-STB could inhibit the tumor growth in animal models.

In summary, we developed a novel shear-thinning biomaterial with the composite of doxorubicin, gelatin and biocompatible silica nanoparticles with various properties. By tuning the properties of silica nanoparticles such as particles size and composition of gelation/silica nanoparticles, the mechanical and rheological properties can be carefully adjusted to meet different requirements. All the compositions used in these experiments are injectable through different sized catheters. The rheological tests showed rapid recovery and mechanical stability with shear-thinning characteristics. Gelatin-Silica nanoparticles-based STBs display superior biological stability, body temperature extrudability, shear-thinning behavior, and rapid network recoverability. These attractive physicochemical properties are favorable for easy administration in vivo, and a gelatin-Silica nanoparticle-based STB may hold great potential in drug delivery, endovascular embolization, tissue regeneration, bioprinting and for other biomedical applications.

REFERENCES

[1] Guvendiren, M., Lu, H. D., Burdick, J. A., Shear-thinning hydrogels for biomedical applications. Soft Matter 2012, 8, 260-272.
[2] Purcell, B. P., Lobb, D., Charati, M. B., Dorsey, S. M., et al., Injectable and bioresponsive hydrogels for on-demand matrix metalloproteinase inhibition. Nat Mater 2014, 13, 653-661.

[3] Jahan, K., Mekhail, M., Tabrizian, M., One-step fabrication of apatite-chitosan scaffold as a potential injectable construct for bone tissue engineering. Carbohyd Polym 2019, 203, 60-70.

[4] Yang, J. A., Yeom, J., Hwang, B. W., Hoffman, A. S., Hahn, S. K., In situ-forming injectable hydrogels for regenerative medicine. Prog Polym Sci 2014, 39, 1973-1986.

[5] Paul, A., Hasan, A., Kindi, H. A., Gaharwar, A. K., et al., Injectable graphene oxide/hydrogel-based angiogenic gene delivery system for vasculogenesis and cardiac repair. ACS Nano 2014, 8, 8050-8062.

[6] Su, D., Jiang, L., Chen, X., Dong, J., Shao, Z., Enhancing the Gelation and Bioactivity of Injectable Silk Fibroin Hydrogel with LAPONITE Nanoplatelets. ACS Appl Mater Interfaces 2016, 8, 9619-9628.

[7] Mulyasasmita, W., Cai, L., Hori, Y., Heilshorn, S. C., Avidity-controlled delivery of angiogenic peptides from injectable molecular-recognition hydrogels. Tissue Eng Part A 2014, 20, 2102-2114.

[8] Whitlow, J., Pacelli, S., Paul, A., Polymeric Nanohybrids as a New Class of Therapeutic Biotransporters. Macromolecular Chemistry and Physics 2016, 217, 1245-1259.

[9] Dawson, J. I., Oreffo, R. O. C., Clay: New Opportunities for Tissue Regeneration and Biomaterial Design. Adv Mater 2013, 25, 4069-4086.

[10] Gaharwar, A. K., Mihaila, S. M., Swami, A., Patel, A., et al., Bioactive Silicate Nanoplatelets for Osteogenic Differentiation of Human Mesenchymal Stem Cells. Adv Mater 2013, 25, 3329-3336.

[11] Tomas, H., Alves, C. S., Rodrigues, J., LAPONITE®: A key nanoplatform for biomedical applications? Nanomed-Nanotechnol 2018, 14, 2407-2420.

[12] Dawson, J. I., Kanczler, J. M., Yang, X. B. B., Pittard, G. S., Oreffo, R. O. C., Clay Gels For the Delivery of Regenerative Microenvironments. Adv Mater 2011, 23, 3304-+.

[13] Gaharwar, A. K., Cross, L. M., Peak, C. W., Gold, K., et al., 2D Nanoclay for Biomedical Applications: Regenerative Medicine, Therapeutic Delivery, and Additive Manufacturing. Adv Mater 2019, 31, e1900332.

[14] Xavier, J. R., Thakur, T., Desai, P., Jaiswal, M. K., et al., Bioactive nanoengineered hydrogels for bone tissue engineering: a growth-factor-free approach. ACS Nano 2015, 9, 3109-3118.

[15] Bhatnagar, D., Xu, D., Gersappe, D., Rafailovich, M. H., Hyaluronic Acid and Gelatin Clay Silica nanoparticles based STB: Substrates for Cell Adhesion and Controlled Drug Delivery. Journal of Chemical and Biological Interfaces 2014, 2, 34-44.

[16] Li, Y. L., Maciel, D., Tomas, H., Rodrigues, J., et al., pH sensitive LAPONITE/alginate hybrid hydrogels: swelling behaviour and release mechanism. Soft Matter 2011, 7, 6231-6238.

[17] Yang, H., Hua, S., Wang, W., Wang, A., Composite hydrogel beads based on chitosan and LAPONITE: preparation, swelling, and drug release behaviour. 2011.

[18] Gaharwar, A. K., Avery, R. K., Assmann, A., Paul, A., et al., Shear-thinning nanosilica nanoparticles based STB for the treatment of hemorrhage. ACS Nano 2014, 8, 9833-9842.

[19] Higuchi, A., Suresh Kumar, S., Benelli, G., Ling, Q.-D., et al., Biomaterials used in stem cell therapy for spinal cord injury. Progress in Materials Science 2019, 103, 374-424.

[20] Hardy, J. G., Lee, J. Y., Schmidt, C. E., Biomimetic conducting polymer-based tissue scaffolds. Curr Opin Biotechnol 2013, 24, 847-854.

[21] Park, H., Temenoff, J. S., Tabata, Y., Caplan, A. I., Mikos, A. G., Injectable biodegradable hydrogel composites for rabbit marrow mesenchymal stem cell and growth factor delivery for cartilage tissue engineering. Biomaterials 2007, 28, 3217-3227.

[22] Avery, R. K., Albadawi, H., Akbari, M., Zhang, Y. S., et al., An injectable shear-thinning biomaterial for endovascular embolization. Sci Transl Med 2016, 8, 365ra156.

[23] Moore, M. J., Malaxos, L., Doyle, B. J., Development of a shear-thinning biomaterial as an endovascular embolic agent for the treatment of type B aortic dissection. J Mech Behav Biomed Mater 2019, 99, 66-77.

[24] Kerativitayanan, P., Tatullo, M., Khariton, M., Joshi, P., et al., Nanoengineered Osteoinductive and Elastomeric Scaffolds for Bone Tissue Engineering. ACS Biomaterials Science & Engineering 2017, 3, 590-600.

[25] Hasany, M., Thakur, A., Taebnia, N., Kadumudi, F. B., et al., Combinatorial Screening of Nanoclay-Reinforced Hydrogels: A Glimpse of the "Holy Grail" in Orthopedic Stem Cell Therapy? ACS Applied Materials & Interfaces 2018, 10, 34924-34941.

[26] Wilson, S. A., Cross, L. M., Peak, C. W., Gaharwar, A. K., Shear-Thinning and Thermo-Reversible Nanoengineered Inks for 3D Bioprinting. ACS Appl Mater Interfaces 2017, 9, 43449-43458.

[27] Samimi Gharaie, S., Dabiri, S. M. H., Akbari, M., Smart Shear-Thinning Hydrogels as Injectable Drug Delivery Systems. Polymers (Basel) 2018, 10.

[28] Sheikhi, A., Afewerki, S., Oklu, R., Gaharwar, A. K., Khademhosseini, A., Effect of ionic strength on shear-thinning nanoclay-polymer silica nanoparticles based STB. Biomaterials Science 2018, 6, 2073-2083.

[29] Ren, Y., Zhao, X., Liang, X., Ma, P. X., Guo, B., Injectable hydrogel based on quaternized chitosan, gelatin and dopamine as localized drug delivery system to treat Parkinson's disease. International journal of biological macromolecules 2017, 105, 1079-1087.

All publications mentioned herein (e.g. the references numerically listed above, and U.S. Patent Publication 20180104059) are incorporated herein by reference to disclose and describe aspects, methods and/or materials in connection with the cited publications.

The Appendix that is included with this provisional application provides invention disclosure that is formatted for publication in a journal. This disclosure shows various aspects and embodiments of the invention. This Appendix is incorporated by reference herein.

The invention claimed is:

1. A composition of matter comprising:
   from 1% (w/w) to 5% (w/w) polymeric gelatin;
   from 1% (w/w) to 5% (w/w) silicate nanoparticles; and
   a therapeutic agent having a molecular weight less than 1000 Daltons; wherein:
   the gelatin, the silicate nanoparticles and the therapeutic agent form a shear thinning hydrogel which provides sustained release of the therapeutic agent for over 15 days.

2. The composition of claim 1, wherein when disposed in an environment having a pH of 7.4, less than 15% or 20% of the therapeutic agent is released from the shear thinning hydrogel over a period of 15 days; and when disposed in an environment having a pH of 5.0, more than 15% or 20% of the therapeutic agent is released from shear thinning hydrogel over a period of 15 days.

3. The composition of claim 2, wherein the therapeutic agent is doxorubicin.

4. The composition of claim 1, wherein the shear thinning hydrogel requires an injection force of at least 5 newtons but less than 30 newtons to extrude the shear thinning hydrogel from a 2.4 Fr Catheter/1 cc syringe.

5. The composition of claim 1, further comprising a human cancer cell.

6. The composition of claim 1, further comprising a pharmaceutical excipient selected from the group consisting of:
a preservative, a tonicity adjusting agent, a detergent, a viscosity adjusting agent, a sugar and a pH adjusting agent.

7. The composition of claim 1, wherein the composition is disposed within a catheter.

8. The composition of claim 1, wherein the silicate nanoparticles comprise synthetic silicate nanoplatelets.

9. A method of delivering the composition of claim 1 to a preselected site, the method comprising:
disposing the composition in a vessel having a first end comprising an opening and a second end;
applying a force to the second end of the vessel, wherein the force is sufficient to liquefy the composition; and
delivering the composition out of the vessel through the opening and to the preselected site.

10. The method of claim 9, wherein the site is an in vivo site.

11. The method of claim 10, wherein the site is at an in vivo location comprising cancerous cells.

12. The method of claim 9, wherein the vessel is a catheter.

13. The method of claim 9, wherein when disposed in an environment having a pH of 7.4, less than 15% or 20% of the therapeutic agent is released from the shear thinning hydrogel over a period of 15 days; and
when disposed in an environment having a pH of 5.0, more than 15% or 20% of the therapeutic agent is released from shear thinning hydrogel over a period of 15 days.

14. The method of claim 13, wherein the therapeutic agent is doxorubicin.

15. The method of claim 9, wherein the shear thinning hydrogel requires an injection force of at least 5 newtons but less than 30 newtons to extrude the shear thinning hydrogel from a 2.4 Fr Catheter/1 cc syringe.

16. The method of claim 9, wherein the composition further comprises a human cancer cell.

17. A method of making the composition of claim 1, comprising combining together the silica nanoparticles, the gelatin, the therapeutic agent having a molecular weight less than 1000 Daltons and optionally a pharmaceutical excipient so as to form the shear thinning hydrogel.

18. The method of claim 17, wherein a relative amount of the silica nanoparticles; and/or a relative amount of the gelatin is selected to tune or modulate one or more rheological properties of the composition and/or a release profile of the therapeutic agent from the shear thinning hydrogel.

* * * * *